(12) United States Patent
Schaefer et al.

(10) Patent No.: US 12,086,910 B2
(45) Date of Patent: Sep. 10, 2024

(54) EFFICIENT MOTION-COMPENSATION IN CONE BEAM COMPUTED TOMOGRAPHY BASED ON DATA CONSISTENCY

(71) Applicant: KONINKLIJKE PHILIPS N.V., Eindhoven (NL)

(72) Inventors: Dirk Schaefer, Hamburg (DE); Christian Haase, Hamburg (DE); Michael Grass, Buchholz in der Nordheide (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 653 days.

(21) Appl. No.: 17/270,712

(22) PCT Filed: Aug. 20, 2019

(86) PCT No.: PCT/EP2019/072192
§ 371 (c)(1),
(2) Date: Feb. 23, 2021

(87) PCT Pub. No.: WO2020/043536
PCT Pub. Date: Mar. 5, 2020

(65) Prior Publication Data
US 2021/0350593 A1 Nov. 11, 2021

(30) Foreign Application Priority Data
Aug. 30, 2018 (EP) .................... 18191715

(51) Int. Cl.
*G06T 11/00* (2006.01)
*A61B 6/40* (2024.01)

(52) U.S. Cl.
CPC .......... *G06T 11/008* (2013.01); *A61B 6/4085* (2013.01); *G06T 2211/412* (2013.01)

(58) Field of Classification Search
CPC .. G06T 11/008; G06T 2211/412; A61B 6/085
See application file for complete search history.

(56) References Cited

U.S. PATENT DOCUMENTS

| 8,437,522 B2 | 5/2013 | Zou et al. |
| 2003/0215051 A1 | 11/2003 | Suzuki |

(Continued)

FOREIGN PATENT DOCUMENTS

| EP | 2074383 B1 | 5/2016 |
| JP | 06114052 A | 4/1994 |
| WO | 2016163719 A1 | 10/2016 |

OTHER PUBLICATIONS

Wang et al., "Locally Linear Embedding-Based Motion Estimation From Truncated Projections for Computed Tomography", IEEE Access, vol. 5, (2017), pp. 11155-11165.

(Continued)

*Primary Examiner* — David Perlman (57) ABSTRACT

An image processing system (IPS), comprising an input interface (IN) for receiving a projection image from a plurality of projection images of a movable object (PAT) acquired along different directions by an imaging apparatus (XA), the projection images defined in a projection domain spanned by a radiation sensitive surface of the detector (D). The system includes a motion checker (MC) configured to operate in the projection domain to decide whether the projection image is corrupted by motion of the object during acquisition.

20 Claims, 5 Drawing Sheets

(56) References Cited

U.S. PATENT DOCUMENTS

| | | |
|---|---|---|
| 2005/0203373 A1 | 9/2005 | Boese |
| 2008/0218510 A1 | 9/2008 | Grass |
| 2009/0169080 A1 | 7/2009 | Noordhoek |
| 2010/0149183 A1 | 6/2010 | Loewke |
| 2011/0123081 A1* | 5/2011 | Sebok .................. G06T 7/33 382/131 |
| 2012/0033868 A1* | 2/2012 | Ren .................. A61B 6/025 378/21 |
| 2013/0051643 A1 | 2/2013 | Jackson |
| 2016/0012613 A1 | 1/2016 | Okerlund |
| 2017/0281112 A1 | 10/2017 | Pack |
| 2018/0182135 A1* | 6/2018 | Lee .................. G06T 11/006 |

OTHER PUBLICATIONS

Feldkamp et al., "Practical cone-beam algorithm", J. Opt. Soc. Am. A, vol. 1, No. 6, (Jun. 1984), pp. 612-619.

Lesaint et al., "Calibration for Circular Cone-Beam CT Based on Consistency Conditions", IEEE Transactions on Radiation an Plasma Medical Sciences, IEEE, vol. 1, No. 6, (Nov. 1, 2017), pp. 517-526.

International Search Report and Written Opinion of PCT/EP2019/072192, dated Oct. 25, 2019.

Clackdoyle, Rolf et al."Overview of Reconstruction Algorithms for Exact Cone-Beam Tomography", Proceedings SPIE, vol. 2299, pp. 230-241, 1994, Abstract Only.

Yu, Hengyong et al "Data Consistency Based Translational Motion Artifact Reduction in Fan-Beam CT", IEEE Transactions on Medical Imaging, vol. 25, No. 6, Jun. 2006, pp. 792-803.

Wang, Ge et al "Preliminary Study on Helical CT Algorithms for Patient Motion Estimation and Compensation" IEEE Transactions on Medical Imaging, vol. 14, No. 2, 1995.

Srinivas, Chukka et al "Motion-Compensated CT Image Reconstruction", Physics in Medicine and Biology, vol. 62, p. 3712, 2017.

Smith, Bruce, "Cone-beam tomography. Recent advances and a tutorial review", Optical Engineering, vol. 29, No. 5, 1990, pp. 524-534.

Lu, Weiguo et al "Tomographic Motion Detection and Correction Directly in Sinogram Space", Physics in Medicine and Biology, vol. 47, 2002, pp. 1267-1284.

Lesaint, Jerome et al "Two Cone-Beam Consistency Conditions for a Circular Trajectory", The 4th International Conf. on Image Formation in Xoray Computed Tomography, 2016, pp. 431-434.

Sisniega, A. et al."Motion compensation in Extremity Cone-Beam CT using a Penalized Image Sharpness Criterion", Physics in Medicine and Biology, vol. 62, 2017, pp. 3712.

* cited by examiner

EFFICIENT MOTION-COMPENSATION IN CONE BEAM COMPUTED TOMOGRAPHY BASED ON DATA CONSISTENCY

CROSS-REFERENCE TO PRIOR APPLICATIONS

This application is the U.S. National Phase application under 35 U.S.C. § 371 of International Application No. PCT/EP20198/072192, filed on Aug. 20, 2019, which claims the benefit of European Patent Application No. 18191715.4, filed on Aug. 30, 2019. These applications are hereby incorporated by reference herein.

FIELD OF THE INVENTION

The invention relates to an image processing system, to a method of image processing, to an imaging arrangement, to a computer program element and to the computer readable medium.

BACKGROUND OF THE INVENTION

Methods to detect patient motion during cone beam CT (computed tomography) scans are mostly based on external sensors today. Techniques which are being used in optical-camera based systems include (but are not limited to) passive and active markers attached to a patient's skin.

Patient motion disturbs in particular cone beam CT imaging since the scan speed is still slow compared to fan beam CT systems. Rigid 3D/2D registration of an initial reconstruction to measured data is a data driven method to estimate rigid motion for every projection image. This data-driven approach takes a significant amount of time, because a 3D forward projection is needed and this operation is computationally expensive. See for instance, A. Sisniega et al, "Motion compensation in extremity cone-beam CT using a penalized image sharpness criterion", Phys. Med. Biol., Vol. 62, 2017. pp. 3712.

SUMMARY OF THE INVENTION

There may therefore be a need for more responsive CT imaging.

The object of the present invention is solved by the subject matter of the independent claims where further embodiments are incorporated in the dependent claims. It should be noted that the following described aspect of the invention equally applies to the image processing method, to the imaging arrangement, to the computer program element and to the computer readable medium.

According to a first aspect of the invention there is provided an image processing system, comprising:
- an input interface for receiving a projection image from a plurality of projection images of a movable object acquired along different directions by an imaging apparatus; and
- motion checker to decide whether the projection image is corrupted by motion of the object during acquisition; and
- a reconstructor configured to reconstruct an image including cross-sectional information of the object based on a decision by the motion checker.

In embodiments, the motion checker is configured to operate, preferably exclusively, in the projection domain where the projection images are defined. The projection domain is spanned by a radiation sensitive surface of the detector. The projection domain is preferably 2D. This allows producing the decision quickly as complex computations in 3D may not be required. The operation of the motion checker may involve computing a measure or score, a number that is, and this measure may then be compared to one or more thresholds to arrive at the decision. Although it is preferable to have the system include the reconstructor, this is not a necessity and there are alternatives envisaged where the output of the motion checker is considered without there necessarily being a reconstruction, such as for teaching purposes or when analyzing motion behavior of the patient.

In embodiments, the measure is configured to measure data consistency. In embodiments, data redundancy is exploited which stems from underlying imaging geometry assumptions. A numeric measure is constructed that is sensitive to violations to the said data redundancy and such violations are deemed to have been caused by patient motion.

In one embodiment, the reconstructor reconstructs the image (such as 3D volume) that includes the cross-sectional information of the object from the plurality of projection images, but wherein the projection image is ignored by the reconstructor if and only if the motion checker decides there is motion corruption.

In one embodiment, the system comprises a motion estimator configured to compute an estimate for the motion if and only if the motion checker decides there is motion corruption.

In one embodiment, system comprises a motion compensator configured to compensate for said motion based on the motion estimate to obtain a motion compensated projection image. Forming of the motion compensated image may include changing the image information (as encoded in the pixels) but may instead include only changing the imaging geometry assigned to the projection image. In other embodiments, both imaging geometry and pixels may be changed.

In preferred embodiments, the computational effort for the motion checker is less than that for the motion estimator and motion compensator. This allows further reducing computation time as the motion estimation and compensation is only performed in respect of motion corrupted projection images. Preferably, the system is modular and the motion checker is arranged as a processing stage distinct from the motion estimator and/or from the motion compensator. Preferably, it is also the motion estimation and motion compensation that are arranged as distinct stages so they can be employed.

In these embodiments, the reconstructor reconstructs the image from at least the motion compensated projection image. The image may be a 3D volume.

In one embodiment, the motion checker computes based on at least two projection images a consistency score that relates to an imaging geometry of the imaging apparatus, the deciding by the motion checker being based on said score.

In one embodiment, the system comprises a visualizer configured to visualize the score value on a display device.

In one embodiment, the object is capable of assuming different physical states and to transition between said physical states.

In one embodiment, the motion checker is configured to decide that there is motion corruption if the projection image was acquired during said transition.

In one embodiment, the motion compensator is configured to apply a corrective action to effect the compensation, wherein the motion compensator is configured to apply the same corrective action to the projection image or another one or more projection images acquired whilst the object is in any one of the physical states. This allows saving even more computation time as the motion estimation may not need to be done anew for projection images individually but can be reused.

According to a further aspect, there is provided a method of image processing, comprising the steps of:
receiving a projection image from a plurality of projection images of a movable object acquired along different directions by an imaging apparatus;
deciding whether the projection image is corrupted by motion of the object during acquisition, and
based on a decision as per the deciding step, reconstructing an image including cross-sectional information of the object.

The projection images are defined in a projection domain spanned by a radiation sensitive surface of the detector and the step of deciding whether the projection image is motion corrupted is, in embodiments, based on one or more operations that are performed in the projection domain. Again, as mentioned above for the system, the reconstruction step may be left out in embodiments.

According to a further aspect, there is provided an image processing arrangement, comprising the imaging apparatus and the system as per any one of the above mentioned embodiments.

According to a further aspect, there is provided a computer program element, which, when being executed by at least one processing unit, is adapted to cause the processing unit to perform the method.

According to a further aspect, there is provided a computer readable medium having stored thereon the program element.

Due to the restriction of the motion correction to motion corrupted projections, the overall robustness of the motion correction is improved. In addition, effects like iso-center or orientation changes due to motion correction, are avoided.

In embodiments, it is proposed an efficient way of performing a 2nd pass motion-compensated reconstruction by performing forward projection and 3D/2D registration only for views actually affected by motion.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
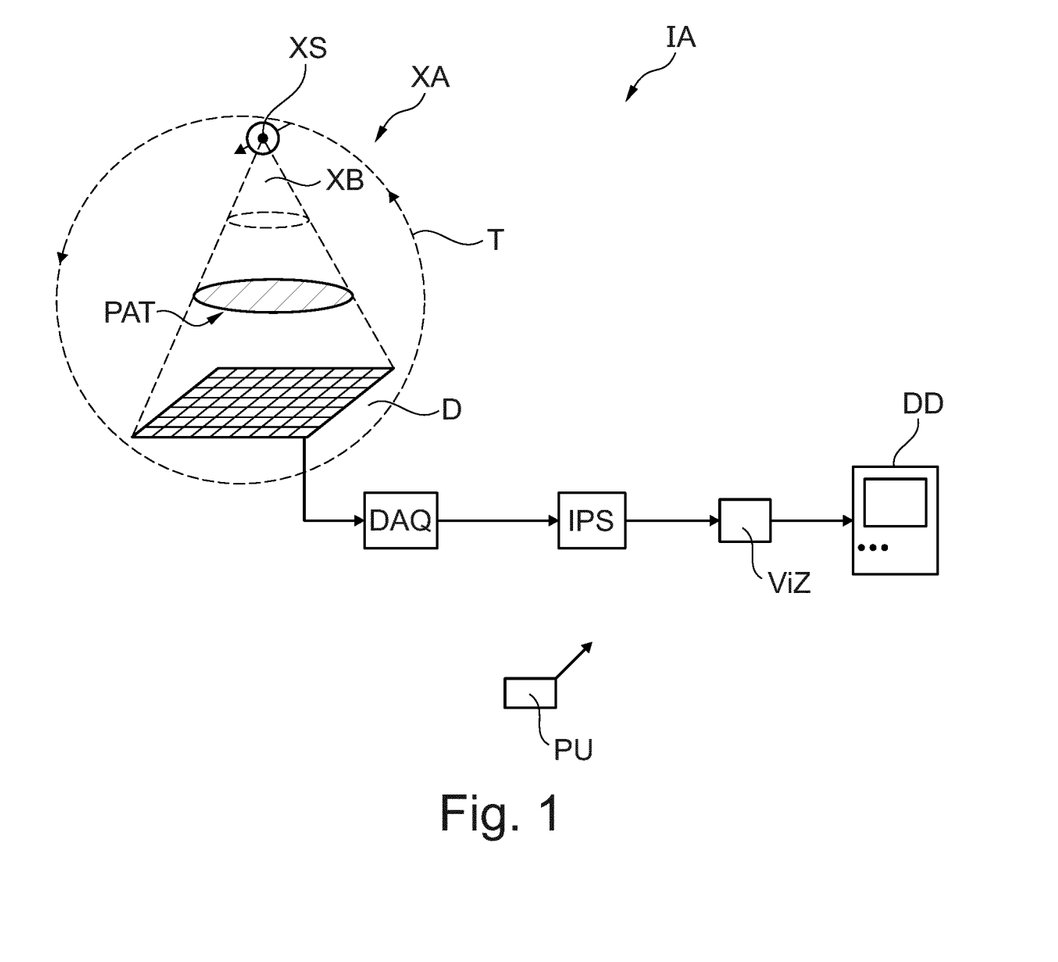
FIG. 1 shows a schematic block diagram of an imaging arrangement.

With reference to FIG. 1, there is shown schematic block diagram of an imaging arrangement IA.

The imaging arrangement IA includes in particular an x-ray imaging apparatus XA ("imager"), preferably a cone beam type CT (computed tomography) scanner, and an imaging processing system IPS. The imaging apparatus may be arranged as a mobile or stationary unit as C- or U-arm scanner or may be arranged in doughnut shaped gantry.

The imaging processing system IPS is configured to process projection imagery π acquired by the x-ray imager XA during image acquisition. The image processing system IPS may be arranged as hardware circuitry and/or software components on a computing unit PU, such as a general purpose computer. The image processing system may be implemented on a workstation usually associated with one or more x-ray imagers XA. In embodiments, a Cloud based architecture is also envisaged wherein the image processing system IPS serves one or more imagers XA. The image processor may be implemented at least in parts as a dedicated hardware component, such as an integrated circuit, FPGA, ASIC. The IPS may be (fully) integrated into the X-ray imager XA. Communication of the projection imagery π from the x-ray imager XA to the image processor IPS may be through a wired or wireless communication network.

When the imager XA is in use, a region of interest (ROI) of a patient PAT is positioned in an examination region between an x-ray source XS and an x-radiation sensitive detection D of the imager XA. During image acquisition, the x-ray source XS is in motion to trace out an orbit or trajectory T around the region of interest. In embodiments, it is also the detector D that traces out the said trajectory in concert with X-ray source XS so as to remain opposite the X-ray source XS during the motion of the x-ray source around the region of interest. Preferably, but not necessarily, the trajectory is at least a part of planar circle or ellipse. The trajectory is not necessarily of closed form.

Alternatively, imagers XA of higher generation are also envisaged herein where the detector D is essentially arranged as a tube or ring in which the patient PAT is situated and it is only the x-ray source that is tracing out the trajectory T in said tube or ring. During motion of the x-ray source XS along trajectory T, an x-ray beam is generated by the X-ray source XS so as to irradiate at least the region of interest. The region of interest may be any anatomic part of the patient PAT, such as head, heart, chest, leg, knee or other.

Because of the cone beam arrangement as preferably envisaged herein, a spatial shape of the beam XB is that of a spatial cone as indicated by the dashed ellipse in FIG. 1. The cone may have circular or elliptic cross-section. Cone beam type is opposed to other types of CT imaging apparatuses where the beam has the shape of a diverging planar fan or where parallel beam geometry is used. In both of these other types, the beam is essentially a 2D structure whilst in cone beam it is 3D.

The x-ray beam XB interacts with patient PAT tissue. As a result, beam XB experiences in particular attenuation, due to absorption, phase shifts/deflection, and types of scatter. Because of this interaction, the x-ray beam XB is modified and egresses the patient at the far side (relative to the location of the x-ray source) to then impinge on the detector sensitive surface of the detector D. The detector surface is a 2D structure.

Detector pixels arranged in rows and columns layout or otherwise form the detector surface and detect the modified radiation. The detection operation by the detector pixels include translating the modified radiation into electrical signals. The electrical signals are converted by a data acquisition unit DAQ into a set of numbers ("projection image values" or "p-values") that form an instance of a digital projection image. As the source XS moves in suitable increments along the trajectory T to assume different spatial positions relative to patient PAT, for each such position, a different projection image (or frame) is detected by the detector. In this manner then a collection of projection images (one or more for each position on the trajectory T) is obtained at the conclusion of the (projection) image acquisition.

Due to the cone beam geometry as mainly (but not exclusively) envisaged herein, each projection image is a two dimensional array of p-values, preferably arranged and stored in a matrix (u,v).

It is possible, but not necessary, for the x-ray source XS to trace out a complete curve (e.g. circle) around the patient. A subtended arc of 180° or less is usually sufficient.

The collection of projection images may be forwarded in to the image processing system IPS. The projection images may be forwarded during the image acquisition as single ones as they are acquired, or they may be so forwarded in different sets at a time, en bloc. Alternatively, all of the projection images are forwarded together at the conclusion of image acquisition.

The image processing system includes in particular a re-constructor RECON. The re-constructor RECON is a software or hardware component that runs a re-construction algorithm suitably adjusted for cone beam type imaging. Broadly, the re-constructor processes the projection imagery and produces the 3D image volume made up from image values called voxels Vx that represent in particular points of internal structures (organs, tissue interfaces, lesions, etc.) inside the patient's PAT body.

Certain views, renderings or cross sections through this volume V may then be produced by suitable reformattor or renderer and may then be passed on to the visualizer VIZ. The visualizer VIZ maps the image values to grey or color values. The visualizer VIZ interacts with graphics circuitry to control a display device DD. A visual representation of the requested cross sectional image or rendering, etc. of the 3D volume may then be displayed on the display device DD to help a user (e.g., a radiologist) in diagnosis or in navigation, intervention planning or other task.

Turning now to the re-constructor RECON component in more detail, this component implements a mapping from the projection imagery to the image volume in 3D. As can be seen from the above, the projection imagery is defined by the pixels that form the radiation sensitive surface of the detector D. This surface is usually plane although this is not necessarily so in all embodiments as curve detectors are also envisaged herein. This detector surface where the projection imagery is defined is called the projection domain. In distinction and addition thereto there is also a second domain which is formed by grid points in the 3D space of the examination region around which the x-ray source and preferably the detector rotate when tracing out the trajectory. The re-constructed image, that is the 3D volume that includes cross sectional images of the ROI, is defined by the voxel values that are assigned to the grid points by the reconstructor RECON as result of the reconstruction. The re-construction operation hence takes as input projection imagery π and computes and assigns image values to the voxel positions in 3D. The image values at the voxel positions so computed together form the reconstructed 3D volume V. Cone beam is different from fan beam or parallel geometry imaging. In the traditional beam geometries, the x-ray source needs to advance along a longitudinal axis of the patient to acquire multiple cross sectional images that then together stack up an image volume. In cone beam CT, imaging is truly or inherently 3D and there is no need to reconstruct individual cross section images and to stack these up. In cone beam CT, once the complete 3D volume is reconstructed, cross sectional images may be computed by relatively straightforward operations such as reformatting or others.

For projection imagery acquired by fan beam or in parallel geometry scanners, traditional filtered back projection (FBP) algorithms can be used to perform the re-construction. Such is not usually the case for cone beam geometry because of the divergent beam geometry. Dedicated cone beam re-construction algorithms have been developed in the past such as that of L. A. Feldkamp et al "*Practical cone-beam algorithm*". J. Opt. Soc. Am. A/Vol 1, No 6, June 1984, or others. It will be understood that although a fan beam geometry is also divergent, this divergence is restricted to a plane whilst this is not the case for the cone beam where there are multiple planes of divergence.

The simpler beam structure of the fan beam or parallel geometry beams allows one to make certain simplifying assumptions when deriving the respective re-construction algorithms. These algorithms, such as FBP, are arrived at through theoretical manipulations of Fourier and Radon transforms. These simplifying assumptions can no longer be made in the cone beam case. However, it has been observed and reported that certain transformations G (to be explained in more detail below) can be applied to the projection data so as to at least approximately transform the cone beam situation to that of a fan beam or parallel geometry case. Bruce Smith has written about this, see for instance "*Cone-beam tomography: recent advances and a tutorial review*", *OPTICAL ENGINEERING*, vol 29 (5), pp 524-534.

Figure 2:
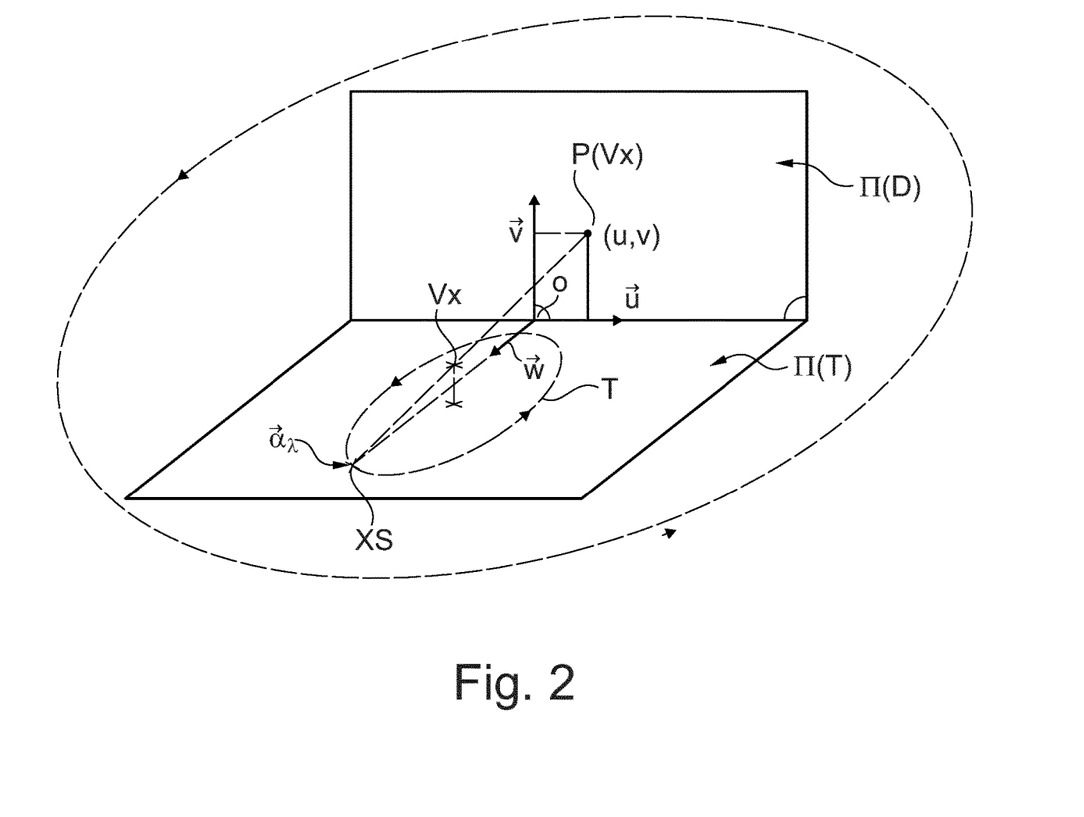
FIG. 2 shows an exemplary imaging geometry for cone beam.

Much of the accuracy of the re-constructed imagery V(π) rests on certain model assumptions in relation to the underlying imaging geometry. One underlying imaging geometry is schematically shown in FIG. 2 so as to better explain these assumptions. FIG. 2 shows in particular a plane Π(T) in which the planar trajectory T of the x-ray source is located. In embodiments this trajectory T is part of a circle, ellipse or other closed curve. Non-planar T's may also be envisaged in embodiments. Although the curves for the T may in themselves be closed, the trajectory T itself is usually not, but instead forms only a part of the curve such as an arc of a circle, etc.

Perpendicular to the plane of the trajectory Π(T) is a plane Π(D) of the detector D. The intersection between the two planes defines one dimension of a 3D co-ordinate system (U, V, W). Another dimension W may be perpendicular to plane Π(D). A point in the detector plane may thus be described by a local co-ordinates (u,v). The origin of the co-ordinate system "0" may be defined at the intersection of U and V with the third dimension w perpendicular to extending in the plane of the trajectory Π(T) and extending towards the location of the x-ray source XS.

The whole coordinate system is subject to move (e.g., rotate) with the X-ray source XS as indicated by the arrows on the surrounding dashed circle. Specifically, FIG. 2 shows the configuration for a given location of the x-ray source XS on the trajectory T. The plane Π(D) represents the central plane that passes through and intersects the region of interest. It will be understood that multiple such planes exist, owing to the cone beam structure of the beam. These planes are parallel to central plane Π(D) and are shifted relative to the central plane in direction −v and +v.

An exemplary voxel point Vx is shown situated on a grid point in 3D space. In this example case for better illustration, the voxel Vx is outside the plane Π(T). A geometrical ray defines the image point P(Vx) of all voxels Vx (only one is shown) along the ray and is recorded by the detector D for a certain location $\alpha_\lambda$ of the x-ray source XS. The location of source XS may be parameterized by vector α, parameterized by location parameter λ. The parameter may be angular. The location (u,v) of the image point P(Vx) on the detector surface Π(D) is the intersection of said geometrical ray with detector surface Π(D). The image value of the image point P(Vx) is the line integral of all voxels (including Vx) that lie on said geometrical ray. The geometrical ray marks the path along which a part of the X-ray beam travels. All geometrical rays (only one is shown) for all voxel Vx together form a spatial cone. The configuration in FIG. 2 define the imaging geometry. The imaging geometry as shown in FIG. 2 defines the spatial relationship between the detector and the x-ray source and their spatial relation to the imaged object, in this case a patient's anatomy or region of interest.

This modeling assumption based on the underlying geometry may for instance require that each projection image π is acquired from a pre-defined source XS position on the trajectory T. There is hence an association between a projection image π and the location parameter λ of source XS. Furthermore, the trajectory T is assumed to have a pre-defined shape which is assumed to be fixed throughout the image acquisition. In case of the exemplary embodiment in FIG. 2, the shape of T may be assumed to be circular or at least a circular arc. Assuming a predefined trajectory may imply a fixed spatial relationship between source and the patient PAT or at least between the source XS and a region of interest ROI.

Unfortunately, these model assumptions are sometimes disturbed due to external factors which may include patient motion. For example, during a brain scan a patient may need to clear their throat. This causes head motion which may occur during the image acquisition whilst the x-ray source XS traces out its path on the predefined trajectory T. When motion happens, the underlying geometry assumptions may no longer apply, or may not be valid throughout the whole acquisition, and imaging artifacts are introduced if not accounted for. For instance, if there is a motion of the region of interest, then there are voxel positions for which the relative trajectory T is no longer circular but has a more a complex, virtual, shape. The underlying modeling assumptions therefore break down and the re-construction algorithm may introduce, at least locally, artifacts which compromise image quality ("IQ").

To alleviate this situation, the proposed imaging system IPS includes a motion composition functionality which allows to compensate or offset for motion corruption that may be incurred during image acquisition.

However, unlike existing motion compensation schemes, the proposed imaging system is selective. In other words, and as discovered by the applicant, during image acquisition it may not be the case that all projection images are corrupted by motion. Not all projection images may therefore need to be motion compensated. For instance, in the mentioned brain imaging case, the disturbance occurs in short bursts throughout the image acquisition. The head motion caused by a coughing attack for instance is something that is a temporally isolated "singularity" and causes abrupt motion peak in a very short span of time. Applicant hence proposes a targeted or selective motion compensation that effects motion compensation only for those projection images that are actually affected by the motion corruption. The remaining projection imagery, not affected by motion, may therefore be retained or at least the motion compensation, if any, may be simplified for some frames of the collection of all projection images. This selective approach allows saving computation time and makes the re-construction more responsive.

Before explaining operation of the image processing system IPS in more detail the following observation may be helpful. From the above discussion of the imaging geometry in FIG. 2 it will become apparent that a projection image includes the following information components: It includes the images values P(Vx) in rows and columns (u,v) as recorded by the detector pixels but it also includes the expected spatial location λ of each image point P(Vx) in the underlying imaging geometry, in particular its relation to the source XS and/or the associated voxel positions Vx along the ray from the source through the ROI to the image point P(Vx). Further geometry information may include, but is not limited to, any one of: the detector position, the detector orientation, the position of the patient table, or the iso-center position. A projection image may hence be written as π=(u,v, λ), with (u,v) the image pixels and λ the 3D spatial coordinate that describes the imaging geometry. Imaging geometry described in particular the location of the source XS in 3D space at acquisition time. Any one projection image at a given instant acquired at a certain source location as is hence a multi-component structure that includes the image information (u,v) and the spatial co-ordinates of its imaging geometry, referred to herein as λ. "λ" may now be used in generic sense and may not necessarily relate to the exemplary, circular geometry of FIG. 2. The spatial information, in particular the spatial co-ordinate λ, may be suitably associated with each projection image such as by encoding into a header file of the respective projection image or other. Alternatively, the spatial information may be separately stored in a memory as files such as calibration data files, or other.

The coordinates λ specify the expected spatial configuration between the respective projection image in space and the ROI. In particular, the coordinates specify the expected spatial constellation between the ROI and the x-ray source XS and/or the detector D.

Figure 3:
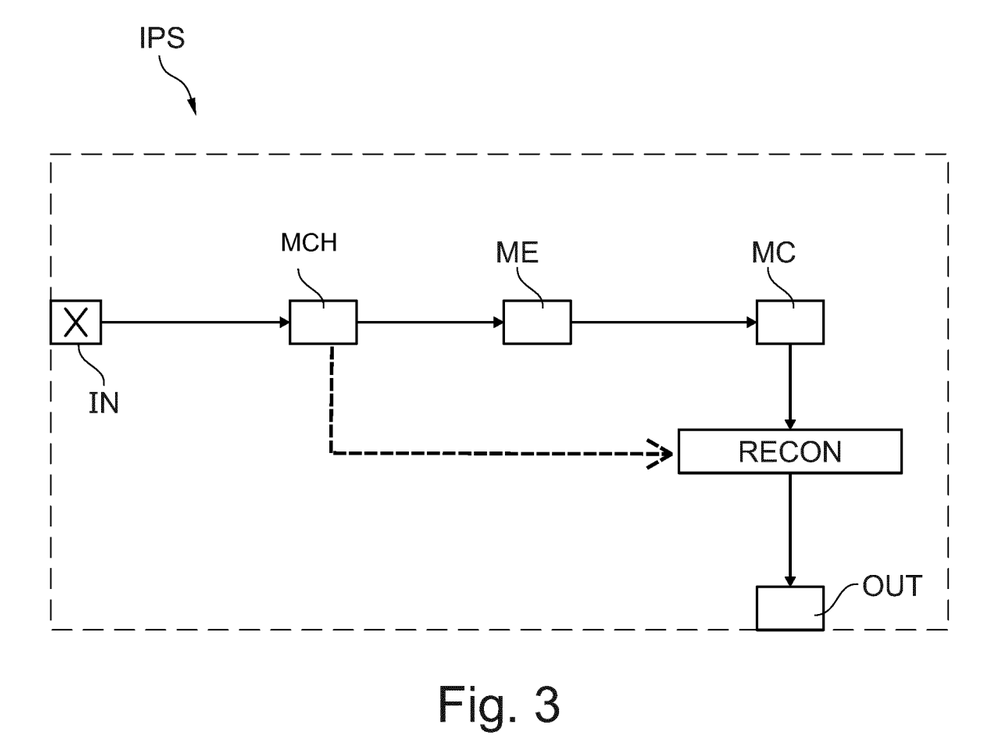
FIG. 3 shows a schematic block diagram for an image processing system.

Referring now to FIG. 3, this shows a schematic block diagram of the image processing system IPS with motion compensation functionality as envisaged herein.

The image processing system includes an input port IN at which the projection imagery π, possibly corrupted by motion, is received from the imager XA preferably after AD conversion. The π may also be retrieved post-imaging from storage such as PACS or other memory.

Each projection image is representable as a matrix of numbers. Each projection image has associated thereto certain spatial coordinates that correspond to the underlying imaging geometry as mentioned above.

Some, or preferably all, the projection images are then processed by a motion checker MCH. The motion checker MCH uses a motion detection measure meas(π) that allows computing a score to establish whether or not a given frame of the projection imagery has been corrupted by motion. In one embodiment, a cone beam data consistency measure meas(·)=DCC(·) is used as reported for instance in Jerome Lesaint et al "*Two cone-beam consistency conditions for a circular trajectory*", presented at the "*4th International Conference on Image Formation in X-Ray Computed Tomography*", 18-22 Jul. 2016, Bamberg, Germany, and as will be explained in more detail below at FIG. 5. In embodiments, the DDC measures the consistency of a frame with some or all other frames that make up the projection imagery. In embodiments, the consistency of the imagery π with the underlying imaging geometry and/or with the assumption of stationary patient is quantified.

The motion corruption measure meas($\pi$) for a given $\pi$ may be a function of additional projection images acquired before and/or after the given projection image $\pi$. Preferably, at least two projection images are processed to produce the score meas($\pi$) for a given projection image $\pi$. For instance, in one embodiment, for a given projection image $\pi_{\lambda,1}$ it is also the subsequent image $\pi_{\lambda,2}$ acquired at a later instant $\lambda_1 < \lambda_2$ that is used to compute a score for the given image $\pi_{\lambda,1}$. More than two follow-up projection images and/or one or more earlier frames may also be included in the computation for a given instant $\pi_{\lambda,1}$. As used herein, an "earlier" or "later" frame may correspond to the location parameter $\lambda$ that defines the location assumed by the X-ray source XS when the projection image was acquired.

A projection image or a set of projection images is deemed motion corrupted if it or they have been acquired during motion of the object. Furthermore, a set of at least two projection images may be considered motion corrupted or inconsistent, if they have been acquired when the object was in two different physical states, respectively. One frame acquired in one state may hence be motion corrupted relative to a frame acquired in the different state of the object. The concept of "states" as used herein will be explained more fully below at FIG. 4B.

Turning now first in more detail to the image processing system IPS, various embodiments of the selective motion compensation are envisaged.

In one of these embodiments, the image processing system IPS is implemented by having the motion checker MCH act as a filter. For instance, in one embodiment, only those projection images that are not motion corrupted will be forwarded to the next stage in the image processing system. Projection images that are decided by the motion checker to include corrupted information due to patient motion are discarded and will not be processed any further by the IPS, in particular will not be used by the reconstructor when reconstructing volume V. In this embodiment the motion checker MCH essentially filters out only those images from the whole set of projection images that are not corrupted by a motion and only these will be passed on in to the re-constructor RECON (dotted line in FIG. 3) to be re-constructed into the 3D volume V. In this embodiment, the reconstructor RECON reconstructs only from a true subset of the original collection of all projection images. The reconstructed volume may then be output at output port OUT and may then be stored, processed for visualization on display device or may be otherwise processed.

In a preferred embodiment, however, motion corrupted projection imagery is not discarded but is further analyzed by passing them on to a motion estimator stage ME. As opposed to the motion checker MCH that is configured to provide an indication of whether or not there is motion corruption, the motion estimator actually computes an estimate $\vec{m}$ of the experienced motion as it pertains to the considered projection image.

This motion estimate is then forwarded on to a motion compensator MC where corrective action is taken in respect of the motion corrupted projection image.

In either of these embodiments, operation of the motion checker may be threshold based. In other words, not all motion corruptions will be deemed equally severe. Based on the threshold, only those projection images are flagged up as motion corrupted that were acquired during a sufficiently substantial motion of the object.

A thresholding may be used by the motion compensator. The motion measure computed by the motion checker is compared against the threshold. For instance, but this is a matter of convention, only if a certain threshold is surpassed, it is deemed to have occurred during a sufficient motion of the imaging object.

The corrective action as performed by the motion compensator may include changing the image information in a frame that is found to be motion corrupted. In other embodiments preferred the image information in the frame is not as such changed but a co-ordinate transformation $Tr^m(u,v,\lambda) = (u',v',\lambda')$ is performed on the associated co-ordinates for that frame, based on the estimated motion $\vec{m}$. In this manner the considered projection image is assigned a new location in space with respect to the imaged object and the trajectory T. Alternatively, $Tr^m(u,v,\lambda) = (u,v,\lambda')$ so the pixel image information (u,v) is maintained, and it is only the spatial imaging geometry coordinate $\lambda$ that is changed $\lambda'$. In some embodiments, the transformation $Tr^m(\cdot)$ may effects a resorting of the images so as to reassign the geometry of one or more of the projection images. In one embodiment, such as in head imaging, two or more projection images may be are reassigned by $Tr^m(\cdot)$ to the same geometry. This may happen for instance, in brain imaging when the patient's PAT head is turned from left to right, say, during image acquisition. Two projection images may hence be acquired from different directions as per $\lambda$, but they represent the same information, the view on the ROI.

The collection of motion corrected projection images together with those frames (if any) that were retained are then forwarded for the re-constructor RECON and are then re-constructed into motion compensated 3D volume which is then output at output port OUT.

In some embodiments there may be a feedback loop between the motion estimator ME, motion compensator MC and the re-constructor RECON. For instance, in one embodiment, the motion estimation by estimator ME includes a 3D/2D registration. In this embodiment a first re-construction is done, knowing that the result may be motion corrupted, to obtain an image volume V' at a first pass. Intermediate volume V' is then forward projected and compared with the projection imagery in the projection domain. If there is deviation, a registration is performed to re-align the projection images and the so re-aligned projection images are then forwarded again in a second pass to the re-constructor. In the second pass the reconstructor RECON then reconstructs from the corrected, that is, re-aligned projection images, together with the remaining, not-corrupted projection images (if any), a motion compensated final 3D volume V.

Embodiments of operation of the proposed image processing system IPS may now be explained with further reference to curves in FIG. 4A, B. In the graphs of FIG. 4A,B, the respective scores DCC are captured over the respective projection image frames shown in exemplary numbering 1-600. The numbering of the projection images is shown along the horizontal axis versus the score values along the vertical axis DCC. Data consistency measure is taken of a central plane for a circular cone beam CT head scan.

FIG. 4A illustrates the inter-play between the motion checker and motion estimator according to one embodiment. The motion checker computes measure DCC($\pi$) for some or each frame $\pi$. The measure is configured to be sensitive to motion corruption. Preferably, the measure DCC can be computed entirely in the projection domain. That is, a "stepping outside", into the surrounding 3D space in which the projection domain is embedded, is not required. In particular, a 3D-to-2D registration is not required for computing the score. More generally, in embodiments, the score can be computed without using information from the surrounding 3D space, other than the geometry information λ.

The scores computed for each projection image frame π may be processed against the threshold as indicated by the area set in right-stroked broad spaced hatchings in FIG. 4A. Frames π whose score exceeds the threshold are then flagged up as motion corrupted and only these are then motion estimated. Of course, in other embodiments, depending on the specific measure used, an inverse situation may occur, where a drop under the threshold is indicative of motion corruption.

The frames that are found to be motion corrupted and for which an individual motion estimate is performed are shown in the lower portion as in FIG. 4A. Such frames are indicated by the left-stroked broad hatchings. Only for these frames a motion compensation is performed based on their respective motion estimate. The remaining projection images (shown in right-stroked narrow hatchings) are left unchanged.

Although the approach as per FIG. 4A is useful and envisaged herein in embodiments, a second embodiment as shown in FIG. 4B is also envisaged, which may be considered a refinement over embodiment FIG. 4A. In this second embodiment, the operation of motion estimation is restricted to certain ones of the frames that are found to be corrupted by motion. A motion, once estimated for a given frame, may be reused for other frames. Specifically, this embodiment is particularly useful when the object to be imaged is capable of assuming different physical states such as the different postures or orientations of a human head, such as left, straight, right. Once a state is assumed, the object may then sojourn a certain period in that respective state, such as when the head rests in a certain position, for example left or right. Once a state is assumed, there is no motion in that period of sojourning in that state. Motion comes into play however when a transition occurs from one state to the other, such as when the head is turned from left to straight or through to right. Respective states may be indicated by plateau regions PL1 and PL2 in the motion corruption score DCC curve. The plateau regions may or may not have different levels.

FIG. 4B illustrates the exemplary situation where the object can assume two different physical states or phases PH1 and PH2. Once a certain phase is assumed, there is no motion in that certain phase for a certain period of time until there is transition back or into another phase as indicated by one, two or more transition regions. In the example in FIG. 4B, three transition regions TR1, TR2, TR3 are shown.

It is proposed herein then to apply individual motion estimation only for projection images that were acquired during such periods of transition TR1, TR or TR3. For projection images acquired whilst the object was sojourning in a given, same, state (as indicated by respective plateaus PL1 and PL2), no individual motion estimation is required. Such projection images whose scores form the plateaus PL1, PL2 are indicated in the lower portion by the section in straight hatchings.

For instance, the motion estimation obtained for one of the projection images from the preceding transition phase TR or TR2 may be used for all projection images in the respective, subsequent plateau region. More specifically, and with reference to plateau region PL2, an individual per frame motion estimation may be performed only for projection images in the preceding transition phase TR2. The motion compensation is performed for the transition region, but the motion estimation may then be reused as is for all projection images in the subsequent plateau region PL2. This can save computation time because no individual estimation needs to be performed in the plateau region. The projection images acquired whilst the ROI sojourns in a given physical state PH1, PH2 may be motion compensated using the same corrective action based on the one, reused motion estimation as computed in preceding transition region. Similar consideration would apply to other plateau regions such as PL1. In these, again, the same motion estimate is used as computed based on projection imagery acquired in the respectively preceding transition region TR2. It will be understood, one of the phases PH1 is a reference or ground phase for which no motion estimate need to be performed. Any projection image acquired in the ground phase PH1 is left unchanged as before in FIG. 4B. When reusing the motion estimate from a transition region, it may be preferable to use the estimate for the latest or last such projection image from the transition phase. It will be understood that the above may be readily generalized to more than two phases and transitions between any two such phases.

Figure 4:
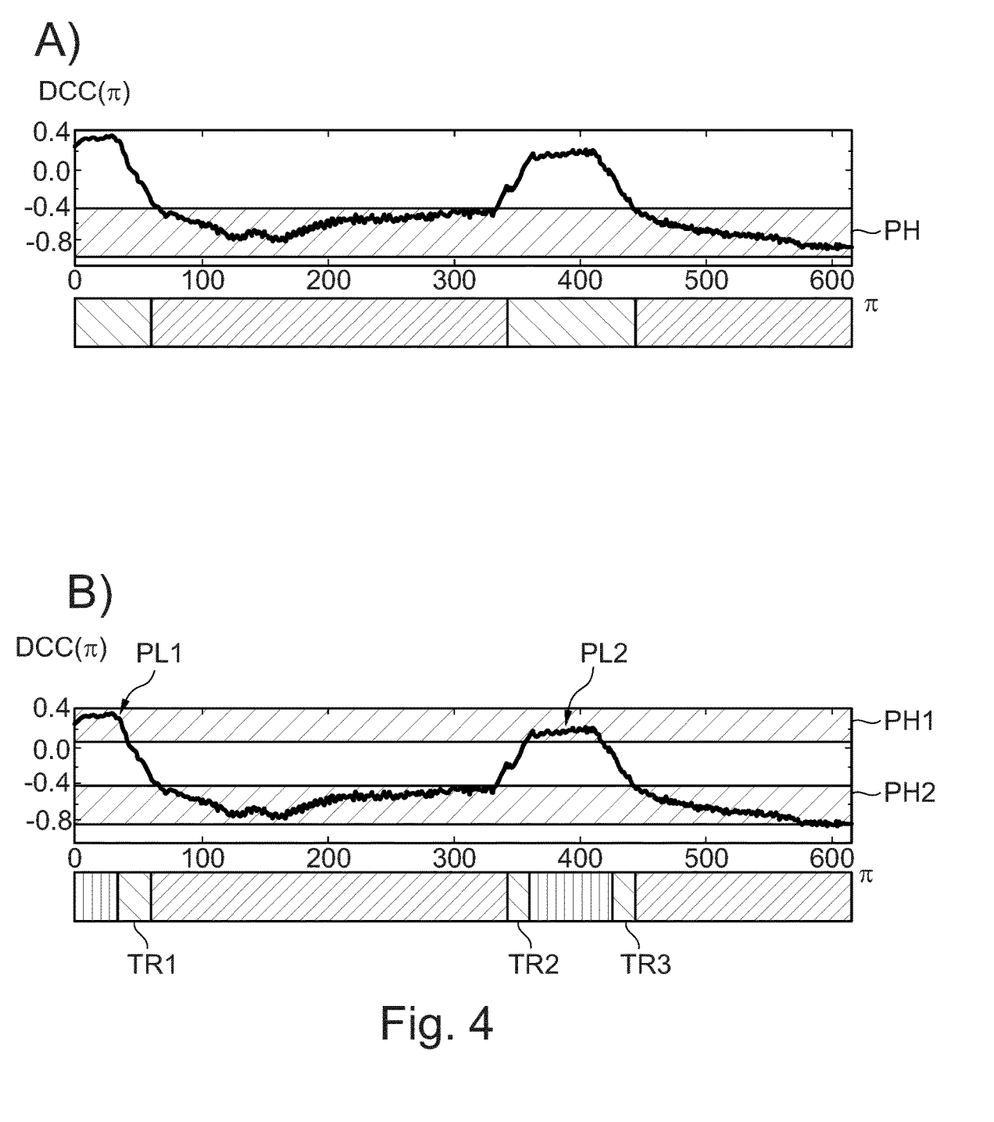
FIG. 4 shows curves of score values for establishing motion corruption.

In embodiments, the score values, as computed over the series of projection images, can themselves be visualized on the display device DD. In embodiments, the visualization may be configured as shown in FIG. 4 A,B. Optionally, a visual indication for the thresholds involved is also indicated as shown in FIG. 4 A,B. The score values visualization furnishes the user with feedback on the amount of motion that occurred during the acquisition. Although the system as proposed herein is fully automatic without need for any user interaction, the user may still be able to interfere by suitable user interface. For instance, based on the visualized score value curve, the user may decide to apply an individual motion correction to certain frames, potentially over-riding the system IPS.

Figure 5:
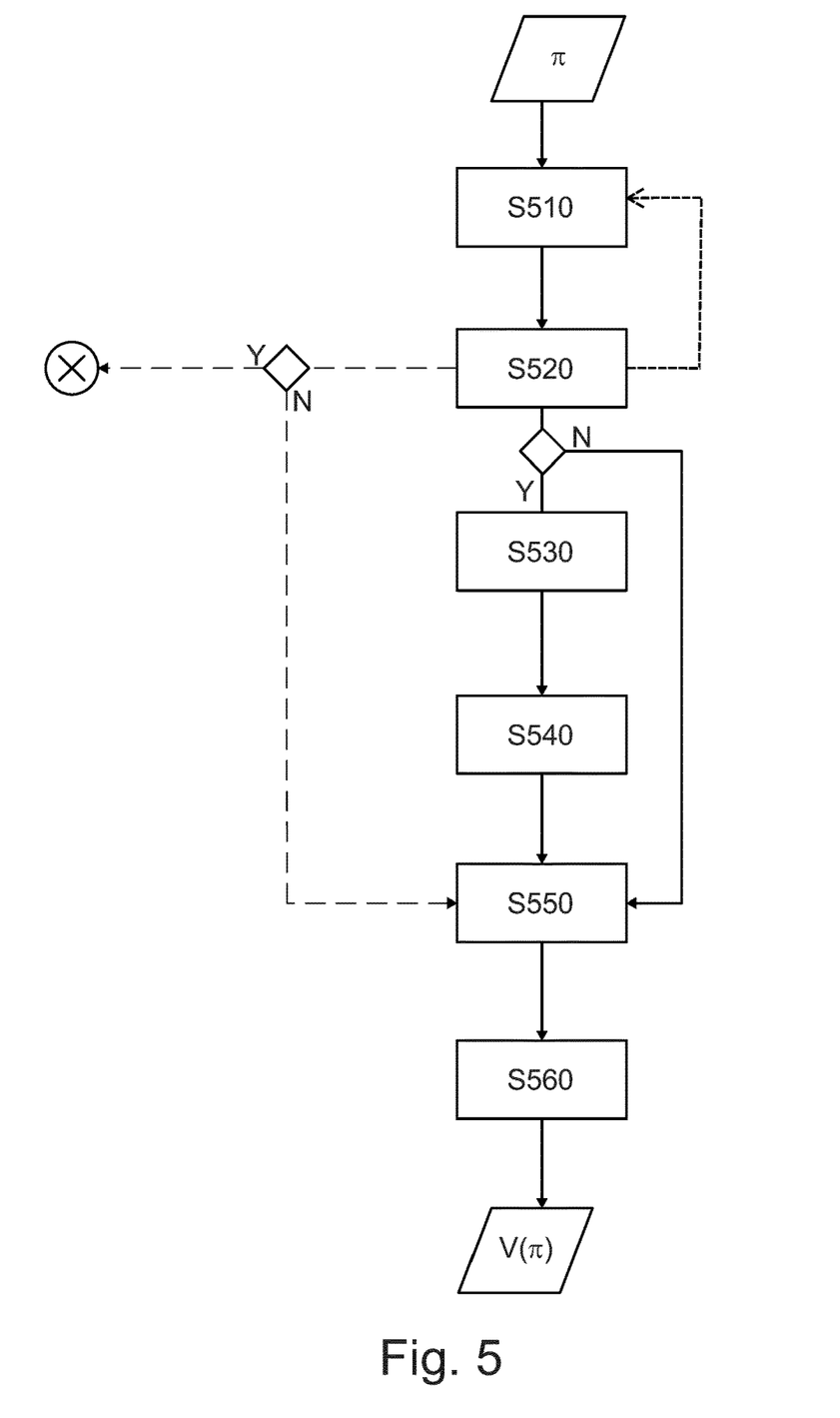
FIG. 5 shows a flow diagram of an image processing method.

Reference is now made to FIG. 5 which shows a flow diagram of the image processing method underlying operation of the image processing system. It will be appreciated however, that the following steps may also be understood as a teaching in their own rights and are not necessarily tied to the architecture of the image processing system IPS as per FIG. 2.

In step S510, projection images are received from the x-ray imaging apparatus, acquired from different directions relative to the region of interest. Alternatively, the projection imagery may also be stored in a memory after acquisition and may be then retrieved therefrom. Preferably, however, the projection imagery is received in real time from the imager XA at a suitable interface IN. The projection imagery comprises the image information in pixels (u,v) and includes spatial information λ about the imaging geometry used in the acquisition. The spatial coordinate of a given projection image represents the position in space of the X-ray source relative to the region. It is the position the X-ray source was assuming when the projection image was acquired. The spatial information may comprise spatial coordinates associated with each projection image. The spatial coordinates may describe a spatial relationship between a location of the respective projection image at acquisition time and the grid points (voxel positions). In cone beam CT imaging, a geometry as illustrated in FIG. 2 may be used. There may also be the assumption that the patient remains stationary relative to the grid points. At least there may be the assumption that any motion that does occur, e.g. moving the patient with the patient table relative to the X-ray system, is predefined or known. If any of these assumptions is not fulfilled, some or all projection images may be motion corrupted due to motion of the patient.

In step S520, the projection images are processed to compute, for some or each projection image, a measure or score. The score is used to decide whether or not there was motion corruption of a given projection image, that is, whether there was patient motion when the respective projection image was acquired. In embodiments, the decision on whether or not there was motion corruption, is based on thresholding by comparing the score against one or more thresholds. The step S520 of computing the measure is preferably performed for a sub-set of all projection images as received at step S510.

In embodiments, one or more projection images may be used to compute the motion corruption score for a given one projection image. The one or more projection images may serve a reference imagery to decide whether the given projection image is consistent with the reference imagery and hence whether or not the given image is motion corrupted. In embodiments, it is envisaged to use as a score data consistency conditions DCC as have been reported elsewhere such as in the above mentioned Lesaint paper. DCCs may be evaluated efficiently by using reformulations as shown by Lesaint and others.

Any suitable measure can be used to compute the score at step S520, so long as it is sensitive to motion. One class of such suitable measures has been found to be DCCs that have been proposed in the past as in the above cited Lesaint reference. In one embodiment, which is however exemplary, the following measure G may be used which can be motivated as follows: Let g-denote the measured X-ray cone-beam transform along a source orbit λ of an attenuating object $f$. Function $f$ is a 3D scalar field that describes the (in general) spatially dependent quality one wishes to reconstruct such as material density, scatter, diffraction (phase contrast) and other. The measured cone beam data π=g for a source position λ is given by:

$$g(\lambda, \vec{\alpha}) = \mathcal{D}f(\lambda, \vec{\alpha}) = \int_0^{+\infty} f(\vec{\alpha}_\lambda + t\vec{\alpha}) dt \qquad (1)$$

at end of the acquisition. In (1), $\vec{\alpha}_\lambda$ is the source XS position, and $\vec{\alpha}_\lambda + t\vec{\alpha}$ is a line from source XS position to the detector plane Π(D) along which the line integral of object $f$ (representing the ROI) is taken.

In embodiments, a measure is used that is based on redundant information and that allows establishing whether redundancy is preserved. In more detail, the redundant information may be represented in a more complex form, for instance as the filtered 2D Radon transform of the measured cone-beam projection g. What is proposed herein in embodiments is to use a functional expression, called G, to measure whether redundancy of information that stems from imaging geometry assumptions is indeed preserved. In embodiments, the information in Radon planes is measured that are expected to include identical information. If the information is not identical, but deviates, this is taken as a measure of data (in-)consistency. A radon plane is a plane into which a Radon transform maps points from the image domain. Put differently, a radon plane is a functional image of a radon transform.

In more detail, in embodiments, data consistency may be measured using a function G (in Lesaint a similar function is referred to as the intermediate function):

$$G(\lambda, \vec{\beta}) = \int_{S^2} h(\vec{\alpha} \cdot \vec{\beta}) g(\lambda, \vec{\alpha}) d\vec{\alpha}, \qquad (2)$$

wherein $\vec{\beta}$ is a vector on the unit sphere $S^2$ in 3D space that determines a plane, such as the central plane. According to the above mentioned Lesaint paper, the relation between G $(\lambda, \vec{\beta})$ and the 3D Radon transform $\mathcal{R}_{\vec{\beta}} f$ is given by $$G(\lambda, \vec{\beta}) = s_h(h * \mathcal{R}_{\vec{\beta}} f)(\vec{\alpha}_\lambda \cdot \vec{\beta}) \qquad (2.1)$$

The convolution kernel h may then be chosen e.g. as ramp or derivative filter:

$$h_R(s) = \int_{\mathbb{R}} |\sigma| e^{2i\pi\sigma s} d\sigma \cdot h_D(s) = \int_{\mathbb{R}} 2i\pi\sigma e^{2i\pi\sigma s} d\sigma. \qquad (3)$$

A plane defined by its normal $\vec{\beta}$ and its distance s to the origin, that contains at least two source positions $\vec{\alpha}_{\lambda,1}$ and $\vec{\alpha}_{\lambda,2}$ provides a consistency measure for the two projections $g(\lambda_1, \vec{\alpha})$ and $g(\lambda_2, \vec{\alpha})$ since from $\vec{\alpha}_{\lambda,1} \cdot \vec{\beta} = \vec{\alpha}_{\lambda,2} \cdot \vec{\beta}$ and equation (2.1) the following identity expression can be derived:

$$G(\lambda_1, \vec{\beta}) = G(\lambda_2, \vec{\beta}). \qquad (4)$$

Identity Expression (4) may hence be used to configure a motion sensitive measure or score, in multiplicative or additive form as required, such as any one of:

$$meas(\lambda_1, \lambda_2) = G(\lambda_1, \vec{\beta}) / G(\lambda_2, \vec{\beta}) \qquad (5)$$

$$meas(\lambda_1, \lambda_2) = \|G(\lambda_1, \vec{\beta}) - G(\lambda_2, \vec{\beta})\| \qquad (6)$$

A combination of (5) or (6), or other functional expression derivable from (4) are also envisaged. In (6), a suitable norm $\|\cdot\|$ may be used. Any measures that differ from (5),(6) by constant factors are understood to be envisaged herein in alternative embodiments. Relation (4), and hence (5),(6), may be numerically efficiently evaluated by using a suitable detector coordinate transformation. In particular, G may be reformulated as three strep processing including projection data pre-weighting, 2D Radon transformation and convolution as reported by Lesaint in the above mentioned reference at page 432, section A). As per (4), (5), (6), the computation may require at one more projection images $(\lambda_2)$ to compute the score for a given projection image at $\lambda_1$. However, a given projection image, say the first, may be chosen as a reference image and expressions (4)-(6) then reduce to a one-variable dependency. The reference projection image(s) may be those acquired during a stationary phase/state representative of the plateau regions in FIG. 4B.

It will be understood that the DCC as per eqs (4)-(6) is merely one exemplary embodiment and other DCCs, in other expression and/or for geometries other than circular are also envisaged herein. In particular, non-radon-plane-based data consistency measures may be used instead in other embodiments. Also, not all measures as envisaged herein may be based on redundant information.

In general, DCCs may be useful to detect a motion corruption if the DCC deviates from a normal value or range of values. Suitably configured thresholds based on said normal values or range may be used to detect such a deviation based on the score computed for the set of projection images. The normal value for the DCC or other measure may not be known outright but can be obtained in one or more calibration scans. The score values as per the DCC function may then be acquired over a series of projection images to get an idea of where the DCC values settle and this may then be taken to represent normal value indicative of no motion. A phantom may be used in the calibration to ensure that there is indeed no motion. More particularly, a Shepp-Logan phantom may be used.

The computing of the score in step S520 may be exclusively performed based on information in the projection domain. No operation in the surrounding 3D space may be required in this step. More specifically, no 3D to 2D registration is required at this step.

In embodiments, the score value that represents the amount of motion corruption as computed in step S520 may be used shown as a graph representation to the user in a suitable display device, for instance as is shown in FIG. 4A,B.

The decision at step S520 on whether or not there is motion corruption determines the subsequent process flow. In one embodiment, if the score (as compared to a threshold) indicates that there was such motion corruption, the respective projection image is discarded and no longer used in subsequent re-construction at step S550. In this embodiment, only a subset of all available projection images is used in the reconstruction step S550 to reconstruct a 3D volume of the ROI.

In alternative embodiments, a projection image, although found to be motion corrupted, may still be used. In these embodiments, the projection image is passed on to step S530 where an estimation of the motion is performed. Projection images that are found to be not motion corrupted are retained as they are and leapfrogged for reconstruction at step S550.

In step S530 an estimate of the motion that caused the corruption is computed. This step may include computing a magnitude and/or direction of the motion. The motion may be estimated by computing a rigid transformation, in particular a 3D rigid transformation.

The motion estimation at step S530 is applied to a given projection image if and only if the previous decision at step 520 is that there is motion corruption.

The so obtained motion estimate is then used in a subsequent step S540 to carry out an actual motion compensation, for which many different embodiments are envisaged, and which will be explained in more detail below.

Step S540 results in motion compensated projection imagery which is then forwarded to step S550 for re-construction. To be sure, the total set of the originally received projection images fall into two groups: those that have been left alone because no sufficient motion corruption was found at step S520 and those for which a motion compensation step has been carried out at step S540. The two groups of projection images, the original ones and motion compensated ones, are then together used in the reconstruction step S550 to produce the 3D volume V which may then be output at step S560 for storage, display or any further processing.

The above described steps S520-S540 are understood to be repeated for some or all projection images from the different directions as received at step S510.

Referring now back in more detail to the motion compensation step S540, the mentioned some embodiments are now described in more detail. In embodiments, the associated corrective action in the motion compensation may include modifying pixel image information (u, v) in projection images. In particular, image information may be changed to effect the compensation, for instance by optical flow methods or other. In other embodiments, however, it is only the spatial imaging geometry co-ordinate λ associated with each projection image that is changed. This change may be done in coordinate transformation $Tr^m(\cdot)$ as mentioned above to account for the patient's motion. In particular, in one embodiment, based on the transformed spatial imaging geometry coordinates of one or more projection images, a virtual trajectory T' is computed and the re-construction is then performed based on that new virtual trajectory. The real, source trajectory T may have been a circular arc, however, relative to the ROI, because of the motion experience, the trajectory may no longer be described as circular but may have a more complex shape which may then be used instead of the circular form to yield a more accurate reconstruction at step S550. In other embodiments or in addition, a 3D-to-2D registration with two passes is performed for motion corrupted projection images.

Preferably, the step S520 for deciding, based on the measure meas(·), whether there was motion corruption is preferably computationally cheaper than any of the subsequent steps of motion estimation S530 and/or motion compensation S540. In particular, the motion checker step S520 is mainly envisaged to not include 3D computations, in particular, no 3D forward projection is required. In this manner, substantial computation time can be saved because the computationally more expensive step of motion estimation S530 and/or motion compensation S540 are only spent on projection images that were actually affected sufficiently severely by motion corruption. Furthermore, parts of the computations in relation to the measure meas( ) such as the DCC condition eqs (4)-(6) may be pre-computed as these parts depend solely on the expected imaging geometry and this is known beforehand. The step S520 of applying meas(·) to the projection data may then be done quickly thus resulting high responsiveness and low CPU time of when computing the meas(·) in decision step S520.

In embodiments, and as is explained in FIG. 4A, a thresholding may be performed at step S520 to decide for which projection images the motion estimation S530 and motion compensation S540 is to be carried out. This embodiment, however, can be further refined by using multiple thresholds, two or more, that allow to distinguish various states of the patient or ROI. In particular, those states of interest where, once assumed, the patient remain relatively calm and it is only in transitions between those states where motion estimation and hence motion compensation is to be carried out. In this embodiment, the acquired time series of score values of the projection imagery may need to be analyzed to identify the plateau regions that represent those stationary states. The stationary states may be indicated by sections of substantially zero gradients. There may be two or more different states corresponding to different plateau levels. The plateau levels may be found by running an automatic differentiator on the score value time series to find the plateaus.

Motion estimation at step S530 is then carried out where there is a non-vanishing gradient which represents a transition. In a further refinement of this embodiment as per FIG. 4B, the actual motion compensation S540 to be applied for projection images associated with the plateau regions may not need to be treated individually. In other words, the same motion compensation S540 may be applied to all projection images associated with the plateau regions. The projection images associated with a given plateau region may be consistent among themselves, but there may be no such consistency relative to projection images taken for a different plateau region. The projection images for one plateau PL1 may hence be judged to motion corrupted relative to projection images for another plateau region PL2. Applying the motion compensation to projection images for one plateau/state then allows establishing consistency with projection images from the another (reference) plateau or state.

Any of the motion estimates computed for projection images acquired during a transition may be used for the plateau region that immediately follows that transition. More specifically, the latest motion estimate computed in the transition region may be used for substantially all the plateau projection images. The motion compensation may then also be the same for the plateau projection images, being based on the same motion estimate. This embodiment allows saving even further computation time as compared to the embodiment where for each projection image that is found to be affected by motion corruption an individual motion estimation/compensation has been carried out as in FIG. 4A. In the embodiment of FIG. 4B, the same motion estimation (estimated for a projection image in the transition region) may be used for all projection images for the subsequent plateau region. No individual estimation need to be performed but the earlier estimation is reused. It is only to motion compensation that need to be applied to the projection images for the plateau region, but this will be same motion compensation as it is based on the same motion estimation.

In embodiments, the proposed method and system may be used to detect and correct the cardio-ballistic effect (CBE) in neuro imaging. The CBE relates to motion caused by heart beat activity and pulse throbbing. The above described principles may be applied to CBE type motion. The motion estimation and compensation may include non-rigid transformations.

In case that the projection images π also include truncated projections, the consistency calculation at step S520 may only be applied to non-truncated planes to avoid additional inconsistency effects that stem from truncations rather than disturbances caused by motion. For good performance, it is proposed herein to avoid mixing these two types of inconsistencies. Alternatively, the consistency measure is augmented to also account for truncation caused inconsistencies.

The proposed method may also be used to identify consistent projections in non-tomographic reconstructions, e.g. for 3D surface modelling from (relatively few) projections.

Although particular reference has been made to CBCT, application of the proposed selective motion compensation to other X-ray imaging modalities other than cone beam are also envisaged and the principles described herein admit direct application thereto.

One or more features disclosed herein may be configured or implemented as/with circuitry encoded within a computer-readable medium, and/or combinations thereof. Circuitry may include discrete and/or integrated circuitry, application specific integrated circuitry (ASIC), a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing system, comprising:
at least one processor in communication with memory, the at least one processor configured to:
receive a projection image from a plurality of projection images of a movable object acquired along a plurality of different directions by an imaging apparatus, the plurality of projection images defined in a projection domain spanned by a radiation sensitive surface of a detector of the imaging apparatus;
determine a decision of whether the projection image is corrupted by motion of the movable object during acquisition based on (i) a consistency measure in relation to an imaging geometry of the imaging apparatus and (ii) an operation in the projection domain; and
reconstruct an image, including cross-sectional information of the movable object, based on the decision.

2. The image processing system of claim 1, wherein the at least one processor is configured to reconstruct the image, including the cross-sectional information of the movable object, from the plurality of projection images, wherein the at least one processor is configured to ignore the projection image for the reconstruction of the image if the decision indicates that the projection image is corrupted by the motion of the movable object.

3. The image processing system of claim 1, wherein the at least one processor is further configured to compute an estimate for the motion of the movable object if the decision indicates that the projection image is corrupted by the motion of the movable object.

4. The image processing system of claim 3, wherein the at least one processor is further configured to compensate for the motion of the movable object based on the motion estimate to obtain a motion compensated projection image.

5. The image processing system of claim 4, wherein the at least one processor is further configured to reconstruct the image based on the motion compensated projection image.

6. The image processing system of claim 1, wherein the at least one processor is further configured to: compute, based on at least two projection images of the plurality of projection images, a consistency score that relates to the imaging geometry of the imaging apparatus and determine the decision based on the consistency score.

7. The image processing system of claim 6, wherein the at least one processor is further configured to visualize a value of the consistency score on a display device.

8. The image processing system of claim 1, wherein the object is capable of assuming a plurality of different physical states and to transition between the plurality of different physical states.

9. The image processing system of claim 8, wherein the at least one processor is further configured to determine the decision that the projection image is corrupted by the motion of the movable object if the projection image was acquired during the transition between the plurality of different physical states.

10. The image processing system of claim 8, wherein the at least one processor is further configured to apply a corrective action to affect a compensation to the motion of the movable object, wherein the at least one processor is configured to apply the corrective action to the projection image or one or more other projection images acquired whilst the movable object is in one of the plurality of different physical states.

11. The image processing system of claim 1, wherein the imaging apparatus is of a cone beam computed tomography type.

12. The image processing system of claim 1, further comprising the imaging apparatus.

13. A method of image processing, the method comprising:
receiving a projection image from a plurality of projection images of a movable object acquired along a plurality of different directions by an imaging apparatus, the plurality of projection images defined in a projection domain spanned by a radiation sensitive surface of a detector of the imaging apparatus;
determining a decision of whether the projection image is corrupted by motion of the movable object during acquisition based on (i) a consistency measure in relation to an imaging geometry of the imaging apparatus and (ii) an operation in the projection domain, and
reconstructing an image, including cross-sectional information of the movable object, based on the decision.

14. The method of claim 13, further comprising ignoring the projection image for the reconstruction of the image if the decision indicates that the projection image is corrupted by the motion of the movable object.

15. The method of claim 13, further comprising computing an estimate for the motion of the movable object if the decision indicates that the projection image is corrupted by the motion of the movable object.

16. The method of claim 13, further comprising compensating for the motion of the movable object based on the motion estimate to obtain a motion compensated projection image used to reconstruct the image.

17. A non-transitory computer-readable storage medium having stored a computer program which, when executed by at least one processor, cause the at least one processor to:
receive a projection image from a plurality of projection images of a movable object acquired along a plurality of different directions by an imaging apparatus, the plurality of projection images defined in a projection domain spanned by a radiation sensitive surface of a detector of the imaging apparatus;
determine a decision of whether the projection image is corrupted by motion of the movable object during acquisition based on (i) a consistency measure in relation to an imaging geometry of the imaging apparatus and (ii) an operation in the projection domain, and
reconstruct an image, including cross-sectional information of the movable object, based on the decision.

18. The non-transitory computer-readable storage medium of claim 17, wherein the instruction, when executed by the at least one processor, further cause the at least one processor to ignore the projection image for the reconstruction of the image if the decision indicates that the projection image is corrupted by the motion of the movable object.

19. The non-transitory computer-readable storage medium of claim 17, wherein the instruction, when executed by the at least one processor, further cause the at least one processor to compute an estimate for the motion of the movable object if the decision indicates that the projection image is corrupted by the motion of the movable object.

20. The non-transitory computer-readable storage medium of claim 19, wherein the instruction, when executed by the at least one processor, further cause the at least one processor to compensate for the motion of the movable object based on the motion estimate to obtain a motion compensated projection image used to reconstruct the image.

* * * * *